(12) United States Patent
Asada et al.

(10) Patent No.: US 9,056,122 B2
(45) Date of Patent: Jun. 16, 2015

(54) METHOD FOR INHIBITION OF BLOOD PHOSPHORUS LEVEL ELEVATION

(71) Applicants: Masanori Asada, Osaka (JP); Tadashi Kanaya, Osaka (JP); Tetsuya Ogawa, Tokyo (JP); Mikiko Shimada, Gunma (JP); Yumi Uehara, Gunma (JP)

(72) Inventors: Masanori Asada, Osaka (JP); Tadashi Kanaya, Osaka (JP); Tetsuya Ogawa, Tokyo (JP); Mikiko Shimada, Gunma (JP); Yumi Uehara, Gunma (JP)

(73) Assignee: Morishita Jintan Co., Ltd., Osaka (JP)

( * ) Notice: Subject to any disclaimer, the term of this patent is extended or adjusted under 35 U.S.C. 154(b) by 129 days.

(21) Appl. No.: 13/688,640

(22) Filed: Nov. 29, 2012

(65) Prior Publication Data

US 2013/0089531 A1    Apr. 11, 2013

Related U.S. Application Data

(63) Continuation of application No. 12/919,344, filed as application No. PCT/JP2009/053837 on Mar. 2, 2009, now abandoned.

(30) Foreign Application Priority Data

Mar. 19, 2008    (JP) .................................. 2008-072218

(51) Int. Cl.
*A61K 35/74*    (2006.01)
*A61K 9/48*    (2006.01)

(52) U.S. Cl.
CPC .............. *A61K 35/74* (2013.01); *A61K 9/4875* (2013.01)

(58) Field of Classification Search
None
See application file for complete search history.

(56) References Cited

U.S. PATENT DOCUMENTS

| | | | |
|---|---|---|---|
| 4,147,773 A * | 4/1979 | Ogasa | 424/93.4 |
| 5,478,570 A | 12/1995 | Sunohara et al. | |
| 5,980,881 A | 11/1999 | Mitsuka et al. | |
| 6,077,504 A * | 6/2000 | Cavaliere ved. Vesley et al. | 424/93.3 |
| 2003/0091530 A1 | 5/2003 | Goto et al. | |
| 2005/0266069 A1 | 12/2005 | Simmons et al. | |
| 2006/0093592 A1 | 5/2006 | Cheruvanky et al. | |
| 2007/0122397 A1 | 5/2007 | Sanguansri et al. | |

FOREIGN PATENT DOCUMENTS

| | | |
|---|---|---|
| CN | 1899314 | 1/2007 |
| JP | 11-199495 | 7/1999 |
| JP | 2000-026304 | 1/2000 |
| JP | 2000-154143 | 6/2000 |
| JP | 2000344802 | 12/2000 |
| JP | 2001002581 | 1/2001 |
| JP | 2001048791 | 2/2001 |
| JP | 2003-012526 | 1/2003 |
| JP | 2004-277296 | 10/2004 |
| JP | 2005-532294 | 10/2005 |
| JP | 2006-176450 | 7/2006 |
| JP | 2007022992 | 2/2007 |
| WO | 03/088984 | 10/2003 |
| WO | 2004-004747 | 1/2004 |

OTHER PUBLICATIONS

Plotnick et al., Compendium, 2007, pp. 1-10.*
Ranganathan et al., The Scientific World Journal, 2005, vol. 5, pp. 652-660.*
Blaut et al., European Journal of Nutrition, 2002, vol. 41, Suppl 1, pp. 1/11-1/16.*
Uniprot.ATCC15707; retrieved from the Internet Apr. 4, 2014 at www.uniprot.org/taxonomy/565042.*
PCT/JP2009/053837; PCT International Search Report dated Apr. 9, 2009.
Folia Pharmacologica Japonica, Nov. 2003, vol. 122, No. 5, pp. 443-453.
Clinical Calcium, 2005, vol. 15, No. 7, pp. 149-154.

* cited by examiner

*Primary Examiner* — Allison Fox
*Assistant Examiner* — Yvonne Pyla
(74) *Attorney, Agent, or Firm* — Renner, Otto, Boisselle & Sklar, LLP

(57) ABSTRACT

The present invention provides a method for inhibiting blood phosphorus level elevation, including administering to a patient in need thereof a composition comprising a lactic acid bacterium as an active ingredient. The method may further include encapsulating the composition comprising a lactic acid bacterium in a capsule. The inhibitor for blood phosphorus level elevation of the present invention is highly safe, is readily administrable, and can sufficiently inhibit a blood phosphorus level elevation.

7 Claims, 1 Drawing Sheet

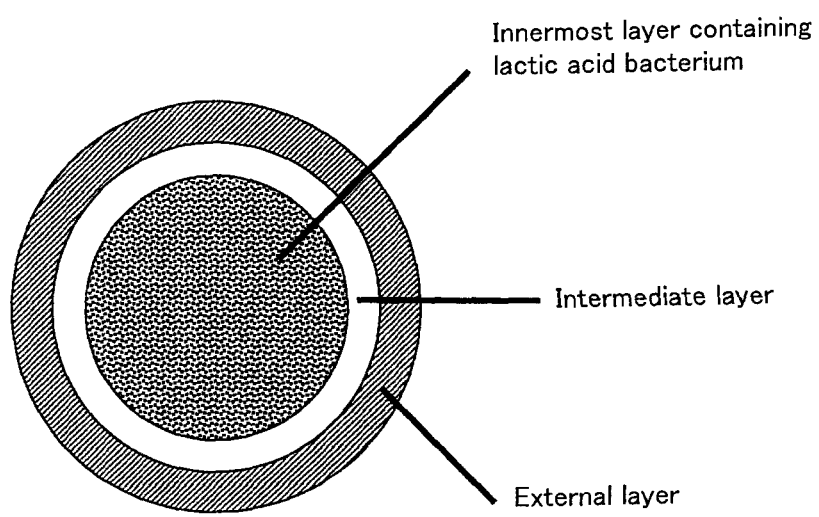

METHOD FOR INHIBITION OF BLOOD PHOSPHORUS LEVEL ELEVATION

CROSS-REFERENCE TO RELATED APPLICATION

The present application is a continuation of and claims priority under 35 U.S.C. §120 to co-pending, commonly-assigned U.S. application Ser. No. 12/919,344, filed 25 Aug. 2010, which is a U.S. national phase application based on International Application No. PCT/JP2009/053837, filed 2 Mar. 2009, which in turn claims priority to Japanese Application No. JP 2008-072218, filed 19 Mar. 2008, the entirety of each of the foregoing priority applications is incorporated herein by reference.

TECHNICAL FIELD

The present invention relates to an inhibitor for blood phosphorus level elevation. More specifically, the present invention relates to an inhibitor for blood phosphorus level elevation effective in the prophylaxis and amelioration of hyperphosphatemia associated with reduced kidney function.

BACKGROUND ART

The kidney plays a very important role in the regulation of phosphorus metabolism. Reduced kidney function would cause hyperphosphatemia due to the build-up of phosphorus in the body. Generally, the blood phosphorus level of a healthy individual is about 2.5 to 4.7 mg/dL. When a blood phosphorus level exceeds 5.5 mg/dL, a treatment (such as, drug administration) is needed to lower the blood phosphorus level.

In the excess phosphorus condition such as hyperphosphatemia, the production and secretion of parathyroid hormone (PTH) are increased, and the growth of accessory thyroid cells is enhanced, thereby inducing secondary hyperparathyroidism. It has been revealed that hyperphosphatemia is involved in the development of renal failure, the onset of cardiovascular complications (for example, phosphorus is bound with calcium in the blood and deposited on the arterial walls, thereby causing arteriosclerosis), and the like. It has been reported that hyperphosphatemia is not only a cause of cardiovascular disorders but also an exacerbating factor to reduce life expectancy for dialysis patients and patients with compromised renal function.

Since a positive correlation is observed between an elevation in PTH level and an increase in fractional phosphate excretion rate, this effect has been believed to be mostly due to increased PTH secretion. However, possible involvement of any components other than PTH has been presented. It has not thoroughly understood for the phosphorus metabolism. Therefore, there is currently no developed, effective blood phosphorus level lowering agent taking advantage of the function of phosphorus metabolism. The removal of phosphorus from the blood relies on dialysis for patients with renal failure who have lost their renal function.

Dialysis patients and patients with impaired renal function often undergo severe dietary restrictions to reduce the intake of phosphorus and the like. However, even with dietary restrictions, they still intake phosphorus of about 1200 mg per day. Since at most about 1000 mg of phosphorus can be removed in one dialysis session, about 3000 mg of phosphorus can be removed in 3 dialysis sessions weekly. Thus, the phosphorus intake is often excessive.

Therefore, dialysis patients and patients with impaired renal function often take a phosphate binder together with dietary restrictions in order to prevent the elevation in blood phosphorus levels. Examples of phosphate binders include those that can adsorb physically phosphorus in the intestinal tract via oral ingestion, including calcium-containing phosphate binders and calcium-free phosphate binders.

However, calcium-containing phosphate binders would lead to excessive intake of calcium to cause the calcium elevation in blood, thereby increasing a risk of cardiovascular disorders. In addition, a calcium-containing phosphate binder, when administered in conjunction with activated vitamin D, cannot be administered in a sufficient amount.

Examples of calcium-free phosphorus binders include ion-exchange resin phosphate binders as disclosed in Patent Documents 1 to 3. However, it is reported that there are side effects such as constipation, abdominal fullness, nausea, and vomiting in ion-exchange resin phosphate binders.

Furthermore, dialysis patients and patients with impaired renal function may be restricted on the intake of not only phosphorus but also potassium, salts, water, and the like. However, sufficient restriction on the intake of phosphorus is difficult in the regard of nutrient intake. Therefore, there is a demand for an effective and safe pharmaceutical preparation.

Attempts have recently been made to develop a blood phosphorus level lowering agent from food materials. Examples of such blood phosphorus level lowering agents include a preparation for hyperphosphatemia which contains as an effective ingredient a galactomannan hydrolysate composed of neutral saccharides (Patent Document 4), a blood phosphorus level lowering agent which contains chitosan oligosaccharides as an effective ingredient (Patent Document 5), and a phosphorus absorption inhibitor which contains a red-alga extract as an effective ingredient (Patent Document 6).

The preparation for hyperphosphatemia which contains as an effective ingredient a galactomannan hydrolysate as disclosed in Patent Document 4 is usually ingested with food, but it seems that the preparation is ingested with water when taken without food. Since dialysis patients are subject to the restrictions on the intake of water, the dosage form of allowing for ingestion without water is preferable to ingest the preparation for hyperphosphatemia.

The blood phosphorus level lowering agent which contains chitosan oligosaccharides as an effective ingredient as disclosed in Patent Document 5 contains oligosaccharide as the principal component, and it would not cause deteriorated mineral absorption in the large intestine. However, it is possible that such a blood phosphorus level lowering agent would cause diarrhea, dehydration, and the like.

The effective ingredient red alga of the phosphorus absorption inhibitor as disclosed in Patent Document 6 can bind strongly to potassium, calcium, iron, magnesium, sodium, and the like to absorb such minerals, which is needed for dialysis patients, thereby causing mineral deficiency. Since mineral level would be varied on dialysis, the phosphorus absorption inhibitor which can absorb minerals is required to be administered carefully for dialysis patients.

It is known that an enteric preparation containing a lactic acid bacterium is administered to reduce neutral fat, uremic substances, and the like in blood for dialysis patients (Patent Document 7). Patent Document 7 discloses that such a preparation ameliorates arteriosclerosis, and ameliorates uremia associated with chronic kidney failure by reducing indoxyl sulfate, phenol, and like substances. However, Patent Document 7 does not make any references to a blood phosphorus level.

Patent Document 8 discloses that a specific type of lactic acid bacterium accumulates phosphorus in the microbial cell in the form of polyphosphoric acid. However, any correlation is made clear in Patent Document 8 between the accumulation of polyphosphoric acid in the microbial cell and blood phosphorus level.

[Patent Document 1] Japanese Laid-Open Patent Publication No. 2001-48791
[Patent Document 2] Japanese Laid-Open Patent Publication No. 9-295941
[Patent Document 3] WO 01/068106
[Patent Document 4] Japanese Laid-Open Patent Publication No. 2007-22992
[Patent Document 5] Japanese Laid-Open Patent Publication No. 2000-344802
[Patent Document 6] Japanese Laid-Open Patent Publication No. 2001-2581
[Patent Document 7] Japanese Laid-Open Patent Publication No. 2004-277296
[Patent Document 8] Japanese Laid-Open Patent Publication No. 2006-176450

DISCLOSURE OF INVENTION

Problems to be Solved by the Invention

It is an object of the present invention to provide an inhibitor for blood phosphorus level elevation that is highly safe, is readily administrable, and can inhibit a blood phosphorus level elevation.

Means for Solving the Problems

The present invention provides an inhibitor for blood phosphorus level elevation comprising a lactic acid bacterium as an active ingredient.

In an embodiment, the lactic acid bacterium is at least one selected from the group consisting of genera *Bifidobacterium*, *Lactobacillus*, *Lactococcus*, and *Enterococcus*.

In an embodiment, the lactic acid bacterium is at least one selected from the group consisting of *Bifidobacterium bifidum*, *B. longum*, *B. infantis*, *B. animalis*, *B. pseudolongum*, *B. dentium*, *Lactobacillus acidophilus*, *L. animalis*, *L. brevis*, *L. bulgaricus*, *L. casei*, *L. delbrueckii*, *L. plantarum*, *Lactococcus lactis* subsp. *lactis*, *Enterococcus faecium*, and *Enterococcus faecalis*.

In one embodiment, the inhibitor for blood phosphorus level elevation is an oral dosage form.

In one embodiment, the inhibitor for blood phosphorus level elevation is at least one form selected from the group consisting of soft capsules, hard capsules, and seamless capsules.

In one embodiment, the inhibitor for blood phosphorus level elevation has acid resistance.

In a further embodiment, the inhibitor for blood phosphorus level elevation is enteric.

In a further embodiment, the inhibitor for blood phosphorus level elevation further comprises an oligosaccharide.

Effects of Invention

The inhibitor for blood phosphorus level elevation of the present invention is highly safe, is readily administrable, and can inhibit a blood phosphorus level elevation for people such as dialysis patients and patients with impaired renal function. Moreover, the inhibitor for blood phosphorus level elevation of the present invention, which contains a lactic acid bacterium, can ameliorate constipation.

BRIEF DESCRIPTION OF DRAWINGS

The drawing is a schematic cross-sectional illustration showing the configuration of a three-layer seamless capsule preparation.

BEST MODE FOR CARRYING OUT THE INVENTION

The inhibitor for blood phosphorus level elevation of the present invention contains a lactic acid bacterium. The "inhibition for blood phosphorus level elevation" refers to reducing a blood phosphorus level, or inhibiting elevation or the rate of elevation in a blood phosphorus level.

Lactic acid bacteria are known to improve the intestinal environment and reduce decomposition products, such as ammonia, indole, and phenol, in the intestines.

Examples of lactic acid bacteria include microorganisms belonging to the genera *Bifidobacterium*, *Lactobacillus*, *Lactococcus*, *Pediococcus*, *Streptococcus*, *Enterococcus*, *Leuconostoc*, *Tetragenococcus*, *Oenococcus*, and *Weissella*. Such microorganisms may be used singly or as a combination of two or more. Among such microorganisms, it is preferable to use those belonging to the genera *Bifidobacterium* and *Lactobacillus*.

Examples of microorganisms belonging to the genus *Bifidobacterium* include *Bifidobacterium bifidum*, *B. longum*, *B. infantis*, *B. animates*, *B. pseudolongum*, *B. dentium*, *B. angulatum*, *B. asteroides*, *B. boum*, *B. catenulatum*, *B. choerinum*, *B. coryneforme*, *B. cuniculi*, *B. gallicum*, *B. gallinarum*, *B. globosum*, *R. indicum*, *B. magnum*, *B. merycicum*, *B. minimum*, *B. parvulorum*, *B. pseudocatenulatum*, *B. pullorum*, *B. ruminale*, *B. ruminantium*, *B. saeculare*, *B. subtile*, *B. suis*, and *B. thermophilum*.

Among such microorganisms belonging to the genus *Bifidobacterium*, it is preferable to use *Bifidobacterium bifidum*, *B. longum*, *B. infantis*, *B. animalis*; *B. pseudolongum*, or *B. dentium*.

Examples of microorganisms belonging to the genus *Lactobacillus* include *Lactobacillus acidophilus*, *L. amylovorus*, *L. animalis*, *L. brevis*, *L. brevis* subsp. *gravesensis*, *L. buchneri*, *L. bulgaricus*, *L. casei*; *L. casei* subsp. *casei*, *L. casei* subsp. *plantarum*, *L. casei* subsp. *tolerans*, *L. cellobiosus*, *L. curvatus*, *L. delbrueckii*, *L. delbrueckii* subsp. *bulgaricus*, *L. delbrueckii* subsp. *delbrueckii*, *L. delbrueckii* subsp. *lactis*; *L. divergens*, *L. fermentum*, *L. fructosus*, *L. gasseri*, *L. hilgardii*, *L. kefir*, *L. leicnmannii*, *L. paracasei*, *L. paracasei* subsp. *paracasei*, *L. pentosus*, *L. plantarum*, *L. reuteri*, *L. rhamnosus*, *L. sakei*, *L. sakei* subsp. *sakei*, *L. sanfrancisco*, *L. vaccinostrcus*, and *Lactobacillus* sp.

Among such microorganisms belonging to the genus *Lactobacillus*, it is preferable to use *Lactobacillus acidophilus*, *L. animalis*, *L. brevis*, *L. bulgaricus*, *L. casei*, or *L. delbrueckii*.

Examples of microorganisms belonging to the genus *Lactococcus* include *Lactococcus lactis*, *L. lactis* subsp. *hordniae*, *L. lactis* subsp. *lactis*, and *L. raffinolactis*.

Among such microorganisms belonging to the genus *Lactococcus*, it is preferable to use *Lactococcus lactis* or *L. raffinolactis*.

Examples of microorganisms belonging to the genus *Enterococcus* include *Enterococcus avium*, *E. casseliflavus*, *E. cecorum*, *E. durans*, *E. faecalis*, *E. faeciurn*, *E. gallinarum*,

*E. hirae, E. malodoratus, E. mundtii, E. pseudoavium, E. raffinosus, E. saccharolyticus, E. seriolicida, E. solitarius,* and *E. villorum.*

Among such microorganisms belonging to the genus *Enterococcus*, it is preferable to use *E. faecalis* or *E. faeciurn*.

The inhibitor for blood phosphorus level elevation of the present invention contains a lactic acid bacterium such that the lactic acid bacterium can be administered in a viable cell count of preferably $5 \times 10^7$ to $5 \times 10^{10}$ and more preferably $1 \times 10^9$ to $1 \times 10^{10}$ per day.

For example, when the inhibitor for blood phosphorus level elevation of the present invention is in the form of a soft capsule, hard capsule, or seamless capsule as described below, a lactic acid bacterium is contained in a viable cell count of preferably $2 \times 10^9$ to $5 \times 10^9$ per gram of a capsule.

The inhibitor for blood phosphorus level elevation of the present invention may further contain an oligosaccharide. The oligosaccharide can assist the growth and the proliferation of the lactic acid bacterium contained in the inhibitor for blood phosphorus level elevation of the present invention.

There is no particular limitation on oligosaccharides for use in the inhibitor for blood phosphorus level elevation of the present invention, and examples include lactulose, raffinose, fructooligosaccharides, galactooligosaccharides, xylooligosaccharides, isomaltooligosaccharides, and mannooligosaccharides.

When the inhibitor for blood phosphorus level elevation of the present invention contains an oligosaccharide, the oligosaccharide is contained in an amount of preferably 50 to 1000 mg and more preferably 100 to 500 mg per 2 billion cells of the lactic acid bacterium contained in the inhibitor for blood phosphorus level elevation of the present invention.

Furthermore, the inhibitor for blood phosphorus level elevation of the present invention may contain, in addition to the lactic acid bacterium and the oligosaccharide, other components such as an excipient, an aroma chemical, and a solvent. Such components include vitamins (such as vitamin A, vitamin B1, vitamin B2, vitamin B6, vitamin B12, vitamin C, vitamin D, vitamin E, pantothenic acid, folic acid, nicotinic acid, inositol, and β-carotene), amino acids (such as glycine, histidine, isoleucine, and glutamic acid), nucleic acids (such as adenine, guanine, thymine, cytosine, uracil, and like nucleobases; adenosine, guanosine, cytidine, thymidine, uridine, and like ribonucleosides, and monophosphate compounds, diphosphate compounds, and triphosphate compounds thereof, deoxyadenosine, deoxyguanosine, deoxycytidine, deoxythymidine, deoxyuridine, and like deoxyribonucleosides, and monophosphate compounds, diphosphate compounds, and triphosphate compounds thereof), minerals (such as calcium, magnesium, iron, zinc, and copper), aliphatic acids (such as α-linoleic acid, eicosapentaenoic acid (EPA), docosahexaenoic acid (DHA), and evening primrose oil), octacosanol, casein digests, water-soluble dietary fiber, insoluble dietary fiber, saccharides (such as starch, cellulose, cornstarch, chitin, chitosan, sucrose, lactose, maltose, and glucose), other useful materials that are approved as food products, food additives, and the like. Such other components may be used singly or as a combination of two or more.

Among such examples, it is preferable to use vitamin C, vitamin E, or β-carotene. For example, vitamin C is contained in an amount of preferably 10 to 500 mg and more preferably 50 to 200 mg per 2 billion cells of the lactic acid bacterium contained in the inhibitor for blood phosphorus level elevation of the present invention. Vitamin E is contained in an amount of preferably 0.5 to 30 mg and more preferably 1.5 to 10 mg per 2 billion cells of the lactic acid bacterium contained in the inhibitor for blood phosphorus level elevation of the present invention. β-Carotene is contained in an amount of preferably 0.5 to 20 mg and more preferably 1 to 5 mg per 2 billion cells of the lactic acid bacterium contained in the inhibitor for blood phosphorus level elevation of the present invention.

Since the inhibitor for blood phosphorus level elevation of the present invention contains a lactic acid bacterium as an active ingredient, it is preferable that the lactic acid bacterium-containing inhibitor is administered orally. In this case, the inhibitor should be designed so that the lactic acid bacterium can travel through the stomach, reach the intestines, and grow therein. Since the pH in the stomach is 1 to 3, most of the lactic acid bacteria orally ingested would be killed by the very low pH. Generally, it is said that no more than $\frac{1}{10000}$ of the amount administered of lactic acid bacteria can reach the intestines while retaining the proliferating ability. Therefore, the influence of gastric acid should be avoided as much as possible so that the lactic acid bacterium in the inhibitor for blood phosphorus level elevation of the present invention can viably reach the human intestines and proliferate therein.

Therefore, it is preferable that the inhibitor for blood phosphorus level elevation of the present invention is in the form of an acid-resistant capsule preparation. The configuration, shape, and the like of the capsule preparation are not particularly limited insofar as the capsule shell is resistant to gastric acid. Examples of the capsule preparation include soft capsules, hard capsules, and seamless capsules. That is, a desirable configuration is such that gastric acid does not penetrate into the capsule or contact the lactic acid bacterium. The capsule shell may be a shell that does not dissolve at pH 4 or less and preferably at pH 1 to 3. There is also no particular limitation on the encapsulation method.

It is further preferable that the inhibitor for blood phosphorus level elevation of the present invention is in the form of an enteric capsule preparation. That is, a preferable form is such that the capsule isolates the capsule content lactic acid bacterium from the outer environment by the shell of capsule in gastric acid, or an acidic fluid having a pH of 1 to 3 and the capsule opens or breaks so that the capsule content lactic acid bacterium can contact with the fluid outside the capsule in the intestinal fluid, or a weakly acidic (neutral) to weakly alkaline fluid having a pH of 5 or greater. The capsule shell may not necessarily dissolve insofar as the lactic acid bacterium in the capsule can contact with the fluid outside the capsule. There is also no particular limitation on the encapsulation method.

Seamless Capsule Preparation

The form of a capsule to impart gastric acid resistance is preferably a seamless capsule. The "seamless capsule" is a type of soft capsule and refers to a capsule of the form in which the content is encapsulated by a seamless shell. It is possible that the seamless capsule has a multilayer structure consisting of two or more layers, and it is preferable that the seamless capsule has a multilayer structure consisting of three or more layers.

Production of a three-layer seamless capsule preparation shall be described below. FIG. 1 is a schematic cross-sectional illustration of a three-layer seamless capsule preparation. This three-layer structure is composed of an innermost layer, an intermediate layer surrounding the innermost layer, and an external layer surrounding the intermediate layer. The innermost layer is composed of a lactic acid bacterium and a non-aqueous solvent or a solid component to form a suspension or a mixture with the lactic acid bacterium (hereinafter this component is referred to as an innermost layer material).

There is no particular limitation on the innermost layer material. Examples include various oils and fats, aliphatic acids, saccharide fatty acid esters, aliphatic hydrocarbons, aromatic hydrocarbons, linear ethers, higher fatty acid esters, higher alcohols, and terpenes. More specifically, examples include, but are not limited to, soybean oil, sesame oil, palm oil, corn oil, cotton seed oil, coconut oil, rapeseed oil, cacao butter, beef tallow, lard, horse oil, whale oil, hydrogenated oils and fats thereof that have a melting point of 40° C. or lower, margarine, shortening, glycerin fatty acid esters, sucrose fatty acid esters, peppermint oil, α-pinene, and D-limonene. Such innermost layer materials may be used singly or as a combination of two or more.

Materials for use in the intermediate layer are those that are mentioned in connection with the innermost layer materials and that have a melting point of 20 to 50° C. but are different from that used in the innermost layer. More preferably, materials that are solid at ordinary temperatures are used. The intermediate layer can serve to inhibit the penetration of fluids and oxygen, preventing any contact with gastric acid. Selection of material can be made according to, for example, the duration of the capsule storage.

Examples of the materials of the external layer (the outermost layer when there are 3 or more layers) include mixtures of proteins and water-soluble polyhydric alcohols, mixtures of proteins, water-soluble polyhydric alcohols, and polysaccharides, and mixtures of polysaccharides and water-soluble polyhydric alcohols. Examples of proteins include gelatin and collagen. Examples of water-soluble polyhydric alcohols include sorbitol, mannitol, glycerol, propylene glycol, and polyethylene glycol. Examples of polysaccharides include agar, gellan gum, xanthan gum, locust bean gum, pectin, alginates, carrageenan, gum arabic, dextrin, modified dextrin, starch, modified starch, pullulan, pectin, and carboxymethylcellulose salts. When pectin, alginates, gellan gum, or carrageenan is used, an alkali metal salt, an alkaline earth metal salt, or the like can be appropriately added.

Production of the above-described three-layer seamless capsule preparation is performed according to a technique well known to those skilled in the art, for example, a dripping method that uses triple nozzles as described in the specification of Japanese Patent No. 1398836. The capsule thus formed is then dried. An example of drying is air drying at ordinary temperature. For example, air drying at a temperature of 5 to 30° C. is commonly practiced. The drying time is preferably 2 to 12 hours. Vacuum drying or freeze drying can be also performed.

To impart acid resistance to the capsule shell of the seamless capsule preparation, an acid resistant external layer is formed, or the shell (outermost layer) of the formed seamless capsule is treated to attain acid resistance.

An example of a method of forming an acid resistant external layer is a method in which pectin, alginates, gum arabic, or the like is added in a proportion of 0.01 to 20 parts by weight and preferably 0.1 to 10 parts by weight per 100 parts by weight of gelatin, agar, carrageenan, or the like that has a gelling ability.

Examples of a method of imparting acid resistance to the shell (outermost layer) of the formed seamless capsule include a cross-linking treatment performed on the external layer (outermost layer) of the seamless capsule and a coating treatment performed on the surface of the seamless capsule. It is preferable to perform such treatments singly or as a combination.

When a protein-containing external layer is subjected to a cross-linking treatment, the seamless capsule is first prepared and thoroughly washed with water. The water-washed seamless capsule is introduced into an aqueous solution that contains a cross-linking agent to cross-link the surface of the external layer. For the cross-linking agent, conventional cross-linking agents are usable, and examples include formaldehyde, acetaldehyde, propionaldehyde, glyoxal, glutaraldehyde, cinnamadehyde, vanillylaldehyde, acetone, ethyl methyl ketone, ethylene oxide, propylene oxide, potassium alum, and ammonium alum. Generally, the treatment of the external layer is performed by introducing 1 part by weight of a seamless capsule into 50 to 100 parts by weight of an aqueous solution containing 0.1 to 2 w/v % and preferably 0.5 to 2 w/v % of a cross-linking agent and stirring for 10 to 300 seconds. The amount of cross-linking agent and the duration of action are varied depending on the cross-linking agent. The surface of the external layer after a cross-linking treatment is thoroughly washed with water to remove the aqueous solution containing the cross-linking agent, and then water contained in the external layer is dried.

For the above-described cross-linking treatment of a protein-containing external layer, cross-linking may be achieved by way of an enzymatic treatment using a transglutaminase. In this case, the external layer is treated by introducing 1 part by weight of the produced seamless capsule into 50 to 100 parts by weight of an aqueous solution containing 0.1 to 10 w/v % and preferably 0.5 to 2 w/v % of an enzyme and stirring for 1 to 300 minutes, and washing and drying are performed in the same manner as described above.

If a coating treatment is performed, the produced wet seamless capsule is dried and then coated according to a commonly used procedure using shellac, ethylcellulose, hydroxypropylmethylcellulose, hydroxypropylcellulose, polyvinyl pyrrolidone, cellulose TC-5, a vinylpyrrolidone-vinyl acetate copolymer, zein, ethylene wax, or the like as a base, and castor oil, rapeseed oil, dibutyl phthalate, polyethylene glycol, glycerol, stearic acid, a fatty acid ester, sorbitan palmitate, polyoxyethylene stearate, acetylated monoglyceride, or the like as a plasticizer.

Furthermore, imparting enteric properties to the capsule protects the lactic acid bacterium present in the capsule from acidic fluids (for example, gastric acid) and the like in the stomach. Imparting enteric properties is performed according to a method commonly employed by a skilled person to produce enteric capsules. In addition, an enteric shell can be provided by use of a mixture containing gelatin and pectin as a material of the external layer of the seamless capsule.

The shape of the seamless capsule preparation may be spherical. The average diameter of the seamless capsule is 0.3 to 10 mm and preferably 1.5 to 8 mm.

The seamless capsule preparation obtained in this manner can be stored at room temperature for six months or longer while maintaining the activity of the lactic acid bacterium, and can be stored for a long period of time of one year or longer when stored at 10° C. or lower.

Soft Capsule Preparation

A soft capsule preparation, as with the seamless capsule preparation, contains a suspension of a lactic acid bacterium in a non-aqueous solvent as its content, enclosed by a shell sheet. The material of the shell sheet is the same as the material of the external layer of the seamless capsule.

The soft capsule preparation can be prepared according to a known technique, for example, the method described in the specification of Japanese Patent No. 2999535. For example, using a rotary die, a shell sheet is passed through the die while injecting and loading the content, and encapsulated by heating. The oil, serving as a release agent, is removed from the resultant soft capsule by washing with a polar solvent (such as methanol, ethanol, propanol, or isopropanol) to release the lactic acid bacterium in the intestines. Thereafter, as is the case with the seamless capsule, a cross-linking treatment and a coating treatment are performed in combination or either of the treatments is performed, in order to attain acid resistance.

The soft capsule preparation may be spherical, spheroidal, or rectangular parallelepiped. A soft capsule having a major axis of 3 to 16 mm and a minor axis of 2 to 10 mm is preferable, and a soft capsule having a major axis of 5 to 7 mm and a minor axis of 2 to 4 mm is more preferable.

The soft capsule preparation obtained in this manner can be stored at room temperature for six months or longer while maintaining the activity of the lactic acid bacterium, and can be stored for a long period of time of one year or longer when stored at 10° C. or lower.

Hard Capsule Preparation

A hard capsule preparation can be produced by molding in advance a capsule shell into a body and a cap, loading the content into the capsule body, and then fitting the capsule cap thereto. Examples of materials of the hard capsule include gelatin, cellulose, pullulan, hydroxypropylmethylcellulose, carrageenan, and cellulose derivatives. The hard capsule can be molded according to a method commonly employed by a skilled person. The molded capsule is also a commercially available. The content can be a thorough mixture of a lactic acid bacterium and an excipient (such as silicic anhydride, synthetic aluminum silicate, lactose, cornstarch, crystalline cellulose), or a powder of dried cells of a lactic acid bacterium. A coating can be provided after loading the content into the capsule. The materials and methods described in connection with the external layer of the seamless capsule are applicable to this coating, thereby imparting acid resistance and preferably collapsibility in the intestines (enteric properties). This coating can also serve to seal the capsule shell to envelope the content.

The hard capsule preparation obtained in this manner can be stored at room temperature for six months or longer while maintaining the activity of the lactic acid bacterium, and can be stored for a long period of time of one year or longer when stored at 10° C. or lower.

The present invention shall be described in detail below by way of examples and comparative examples, but the present invention is not limited to the examples.

EXAMPLES

Example 1

The seamless capsule containing *bifidobacterium* was prepared as described below using capsule production apparatus equipped with triple concentric nozzles.

The cell powder of *Bifidobacterium* (*Bifidobacterium longum* subspecies *longum* JCM1217) in an amount of 100 g was dispersed in hydrogenated oil prepared by melting 400 g of hydrogenated palm kernel oil having a melting point of 34° C. This dispersion was discharged from the inner nozzle of the triple concentric nozzles, hydrogenated oil prepared by melting hydrogenated palm kernel oil having a melting point of 43° C. was discharged from the intermediate nozzle disposed around the inner nozzle, and a gelatin solution (a solution prepared by dissolving 600 g of gelatin, 300 g of glycerol, and 100 g of pectin in 4 kg of purified water) was discharged from the outermost nozzle simultaneously into rapeseed oil flowing as a fluid carrier under cooling (15° C.) in order to prepare the three-layer seamless capsule containing *bifidobacterium*, having a diameter of 2.0 mm (2 billion cells of *bifidobacterium* per 0.2 g of seamless capsule).

34 dialysis patients (hereinafter sometimes simply referred to as patients) ingested 0.2 g of the *bifidobacterium*-containing seamless capsule thus prepared daily over 4 weeks. The patients did not take any other blood phosphorus level lowering agents. While under dietary instructions by a dietitian, not all patients had the same meals.

Blood was collected before the ingestion of the *bifidobacterium*-containing seamless capsule and 1 week, 3 weeks, and 4 weeks after the beginning of ingestion, and blood phosphorus levels were measured according to the molybdenum blue method using a Phospha C-Test Wako for inorganic phosphorus measurement (manufactured by Wako Pure Chemical Industries, Ltd.).

Tables 1 and 2 show the results of measuring the blood phosphorus level of each patient. In addition, Table 3 shows the results of measuring the blood phosphorus levels of 11 patients who did not take either the *bifidobacterium*-containing seamless capsules or any other blood phosphorus level lowering agents (control group).

TABLE 1

| | Blood phosphorus level (mg/dL) | | | |
|---|---|---|---|---|
| | Before ingestion | 1 week after the beginnig of ingestion | 3 weeks after the beginnig of ingestion | 4 weeks after the beginnig of ingestion |
| Patient 1 | 6.35 | 5.8 | 5.9 | 4.7 |
| Patient 2 | 6.08 | 4.9 | 5.5 | 4.5 |
| Patient 3 | 5.53 | 5.1 | 5.0 | 4.1 |
| Patient 4 | 6.08 | 4.7 | 3.9 | 4.9 |
| Patient 5 | 5.93 | 5.0 | 4.8 | 4.8 |
| Patient 6 | 8.25 | 6.1 | 7.0 | 6.7 |
| Patient 7 | 6.53 | 6.2 | 6.3 | 5.8 |
| Patient 8 | 5.48 | 4.2 | 3.6 | 4.9 |
| Patient 9 | 6.15 | 5.7 | 5.2 | 5.7 |
| Patient 10 | 7.23 | 7.5 | 7.2 | 6.7 |
| Patient 11 | 6.58 | 6.1 | 5.9 | 6.1 |
| Patient 12 | 6.80 | 6.6 | 7.9 | 6.4 |
| Patient 13 | 5.80 | 6.2 | 6.1 | 5.6 |
| Patient 14 | 7.33 | 5.9 | 6.3 | 7.1 |
| Patient 15 | 6.48 | 4.4 | 5.6 | 6.3 |
| Patient 16 | 7.18 | 6.3 | 7.4 | 7.1 |
| Patient 17 | 8.13 | 4.8 | — | 8.1 |

TABLE 2

| | Blood phosphorus level (mg/dL) | | | |
|---|---|---|---|---|
| | Before ingestion | 1 week after the beginnig of ingestion | 3 weeks after the beginnig of ingestion | 4 weeks after the beginnig of ingestion |
| Patient 18 | 5.80 | 5.5 | 6.1 | 5.8 |
| Patient 19 | 6.88 | 5.9 | 7.5 | 6.9 |
| Patient 20 | 6.53 | 5.4 | 5.9 | 6.6 |
| Patient 21 | 8.43 | 8.0 | 9.5 | 8.6 |
| Patient 22 | 5.68 | 5.8 | 5.5 | 5.8 |
| Patient 23 | 6.45 | 8.0 | 6.6 | 6.7 |
| Patient 24 | 5.93 | 5.3 | 5.7 | 6.2 |
| Patient 25 | 6.63 | 5.5 | 6.1 | 7.0 |
| Patient 26 | 6.15 | 6.2 | 7.6 | 6.5 |
| Patient 27 | 6.15 | 5.4 | 6.5 | 6.7 |
| Patient 28 | 6.47 | 7.2 | 6.4 | 7.1 |
| Patient 29 | 7.83 | 8.1 | 8.5 | 8.7 |
| Patient 30 | 6.40 | 6.9 | 7.1 | 7.3 |
| Patient 31 | 7.45 | 8.0 | 9.4 | 8.5 |
| Patient 32 | 5.37 | 6.2 | 6.2 | 6.6 |
| Patient 33 | 6.83 | 7.7 | 7.0 | 8.5 |
| Patient 34 | 8.23 | 9.6 | 8.8 | 10.9 |

TABLE 3

| | Blood phosphorus level (mg/dL) | | | |
|---|---|---|---|---|
| | Before ingestion | 1 week after the beginnig of ingestion | 3 weeks after the beginnig of ingestion | 4 weeks after the beginnig of ingestion |
| Patient 35 | 8.25 | 8.4 | 9.0 | 9.5 |
| Patient 36 | 6.12 | 5.9 | 5.9 | 7.4 |
| Patient 37 | 6.96 | 6.7 | 7.4 | 7.5 |
| Patient 38 | 7.33 | 7.9 | 7.9 | 8.0 |
| Patient 39 | 7.35 | 7.1 | 7.0 | 8.5 |
| Patient 40 | 5.97 | 6.2 | 6.1 | 6.3 |
| Patient 41 | 6.20 | 6.7 | 6.6 | 6.9 |
| Patient 42 | 7.69 | 8.2 | 8.4 | 10.7 |
| Patient 43 | 6.85 | 6.6 | 6.9 | 8.3 |
| Patient 44 | 7.94 | 7.7 | 7.6 | 9.8 |
| Patient 45 | 7.92 | 8.0 | 8.7 | 9.2 |
| Average | 7.1 | 7.2 | 7.4 | 8.4 |

Average increase in blood phosphorus level for 4 weeks: 1.3 mg/dL

As seen from the values indicating the blood phosphorus levels before the ingestion and after 4 weeks of the beginning of ingestion of the *bifidobacterium*-containing seamless capsules presented in Tables 1 and 2, the average increase in blood phosphorus level for the 34 patients was −0.04 mg/dL (i.e., the average blood phosphorus level was reduced by 0.04 mg/dL).

As shown in Table 1, it can be understood that for the 17 patients, the blood phosphorus levels 4 weeks after the ingestion of the *bifidobacterium*-containing seamless capsules were lowered compared to their blood phosphorus levels before the ingestion of the *bifidobacterium*-containing seamless capsules.

On the other hand, as shown in Table 2, for the remaining 17 patients, the blood phosphorus levels were not lowered by the ingestion of the *bifidobacterium*-containing seamless capsule. However, since the average blood phosphorus level was reduced by 0.04 mg/dl for the 34 patients, it can be understood that a blood phosphorus level elevation was inhibited.

For the control group, the blood phosphorus levels after treatment were significantly higher than the levels before treatment (Paired T-test: p<0.01), although no significant increase was observed for the treated group. Therefore, it can be understood that the *bifidobacterium*-containing seamless capsule obtained in Example 1 significantly inhibit a blood phosphorus level elevation.

Example 2

The cell powder of *Bifidobacterium* (*Bifidobacterium longum* subspecies *longum* JCM1217) in an amount of 50 g was suspended in 300 g of rapeseed oil to prepare the content fluid of soft capsule. Next, 400 g of gelatin and 100 g of glycerol were added to 200 g of distilled water and dissolved by stirring at 60° C., and the solution was molded into a sheet to obtain gelatin films. Next, the gelatin films were fed between a pair of rotary cylindrical metal molds while the content fluid was injected between the gelatin films with a pump operating in concert with the molds in order to prepare the soft capsule (2 billion cells of *bifidobacterium* per soft capsule).

30 dialysis patients ingested 1 capsule of the *bifidobacterium*-containing soft capsule thus prepared daily over 4 weeks. The condition of ingestion was the same as that in Examples 1. The patients did not take any other blood phosphorus level lowering agents. While under dietary instructions by a dietitian, not all patients had the same meals.

Blood was collected before and 4 weeks after the beginning of the ingestion of the *bifidobacterium*-containing soft capsules, and blood phosphorus levels were measured. Table 4 shows the results.

For 15 patients who did not take either the *bifidobacterium*-containing soft capsules or any other blood phosphorus level lowering agents (control group), the average blood phosphorus level before treatment was about 7.10 mg/dL, and the average blood phosphorus level four-week after treatment was about 8.30 mg/dL (for the control group, the average increase in blood phosphorus level was 1.21 mg/dL).

TABLE 4

| | Blood phosphorus level (mg/dL) | |
|---|---|---|
| | Before ingestion | 4 weeks after the beginnig of ingestion |
| Patient 1 | 5.7 | 5.1 |
| Patient 2 | 8.1 | 7.5 |
| Patient 3 | 8.3 | 7.9 |
| Patient 4 | 6.3 | 5.9 |
| Patient 5 | 7.1 | 7.0 |
| Patient 6 | 8.0 | 7.9 |
| Patient 7 | 7.2 | 7.2 |
| Patient 8 | 7.0 | 7.0 |
| Patient 9 | 6.0 | 6.5 |
| Patient 10 | 6.7 | 7.4 |
| Patient 11 | 6.0 | 6.7 |
| Patient 12 | 6.0 | 6.8 |
| Patient 13 | 7.6 | 8.4 |
| Patient 14 | 7.2 | 8.2 |
| Patient 15 | 8.4 | 9.6 |
| Patient 16 | 7.3 | 8.7 |
| Patient 17 | 6.0 | 7.3 |
| Patient 18 | 8.2 | 9.6 |
| Patient 19 | 6.1 | 7.6 |
| Patient 20 | 5.7 | 7.2 |
| Patient 21 | 7.0 | 8.6 |
| Patient 22 | 8.3 | 10.0 |
| Patient 23 | 7.6 | 9.3 |
| Patient 24 | 7.5 | 9.3 |
| Patient 25 | 5.5 | 7.3 |
| Patient 26 | 6.0 | 7.9 |
| Patient 27 | 6.7 | 8.6 |
| Patient 28 | 7.2 | 9.2 |
| Patient 29 | 8.0 | 10.0 |
| Patient 30 | 5.9 | 8.0 |

Rate of patients with reduced blood phosphorus level: 20% (6 patients)
Average increase in blood phosphorus level for patients 1 to 30: 0.97 mg/dL
Average increase in blood phosphorus level for control group: 1.21 mg/dL As shown in Table 4, it can be understood that 6 (patients 1 to 6) of the 30 patients had lowered blood phosphorus levels after the ingestion of the *bifidobacterium*-containing soft capsule. On the other hand, lowering of the blood phosphorus level was not observed after the ingestion of the *bifidobacterium*-containing soft capsule for the remaining 24 patients. The average increase in blood phosphorus level was 0.97 mg/dL for the 30 patients compared to the increment for the control group of 1.21 mg/dL, and it can be understood that a blood phosphorus level elevation was inhibited.

Example 3

A coating was applied to the soft capsule as obtained in Example 2 according to the method described in Japanese Laid-Open Patent Publication No. 2003-230363.

First, an immersion fluid containing 20 parts by weight of shellac, 2 parts by weight of triethyl citrate, and 78 parts by weight of ethanol was prepared. Next, the soft capsule as obtained in Example 2 was immersed in the immersion fluid thus prepared, and subject to air-drying at about 15 to 20° C. such that the viable cell count of the *bifidobacterium* was not reduced. The immersion and drying treatment was repeated 3 times, in order to prepare the shellac-coated soft capsule containing *bifidobacterium* (enteric *bifidobacterium*-containing soft capsule).

30 dialysis patients ingested 1 capsule of the enteric *bifidobacterium*-containing soft capsule thus prepared daily under the same conditions of ingestion as in Example 1. Blood was collected before and 4 weeks after the beginning of the ingestion of the enteric *bifidobacterium*-containing soft capsule, and blood phosphorus levels were measured. Table 5 shows the results.

For 15 patients who did not take either the enteric *bifidobacterium*-containing soft capsules or any other blood phosphorus level lowering agents (control group), the average blood phosphorus level before treatment was about 6.86 mg/dL, and the average blood phosphorus level four-week after treatment was about 8.02 mg/dL (for the control group, the average increase in blood phosphorus level was 1.15 mg/dL).

TABLE 5

| | Blood phosphorus level (mg/dL) | |
|---|---|---|
| | Before ingestion | 4 weeks after the beginnig of ingestion |
| Patient 1 | 6.0 | 4.7 |
| Patient 2 | 7.5 | 6.1 |
| Patient 3 | 5.7 | 4.4 |
| Patient 4 | 7.7 | 6.6 |
| Patient 5 | 6.6 | 5.6 |
| Patient 6 | 8.0 | 7.0 |
| Patient 7 | 5.5 | 4.6 |
| Patient 8 | 8.2 | 7.4 |
| Patient 9 | 8.1 | 7.2 |
| Patient 10 | 5.4 | 4.7 |
| Patient 11 | 6.4 | 5.7 |
| Patient 12 | 6.4 | 5.7 |
| Patient 13 | 7.9 | 7.7 |
| Patient 14 | 8.3 | 8.2 |
| Patient 15 | 7.8 | 8.0 |
| Patient 16 | 7.4 | 7.7 |
| Patient 17 | 5.9 | 6.3 |
| Patient 18 | 7.8 | 8.3 |
| Patient 19 | 7.9 | 8.7 |
| Patient 20 | 8.1 | 9.1 |
| Patient 21 | 5.5 | 6.5 |
| Patient 22 | 7.7 | 8.7 |
| Patient 23 | 7.1 | 8.2 |
| Patient 24 | 7.7 | 8.8 |
| Patient 25 | 5.8 | 7.1 |
| Patient 26 | 7.6 | 8.9 |
| Patient 27 | 8.3 | 9.7 |
| Patient 28 | 8.0 | 9.4 |
| Patient 29 | 6.8 | 8.3 |
| Patient 30 | 5.7 | 7.2 |

Rate of patients with reduced blood phosphorus level: 47% (14 patients)
Average increase in blood phosphorus level for patients 1 to 30: 0.13 mg/dL
Average increase in blood phosphorus level for control group: 1.15 mg/dL As shown in Table 5, it can be understood that 14 (patients 1 to 14) of the 30 patients had lowered blood phosphorus levels after the ingestion of the enteric *bifidobacterium*-containing soft capsule. On the other hand, lowering of the blood phosphorus level was not observed after the ingestion of the *bifidobacterium*-containing soft capsule for the remaining 16 patients. The average increase in blood phosphorus level was 0.13 mg/dL for the 30 patients compared to the increment for the control group of 1.15 mg/dL, and it can be understood that a blood phosphorus level elevation was inhibited.

For the control group, the blood phosphorus levels after treatment were significantly higher than the levels before treatment (Paired T-test: p<0.01), although no significant increase was observed in the treated group. Therefore, it can be understood that the enteric *bifidobacterium*-containing soft capsule obtained in Example 3 significantly inhibit a blood phosphorus level elevation.

Example 4

The cell powder of *bifidobacterium* (*Bifidobacterium longum* subspecies *longum* JCM1217) was loaded into a commercial hard capsule having a size according to the Japanese Pharmacopoeia of 5 in 2 billion cells of *bifidobacterium* per 1 hard capsule to prepare the hard capsule containing *bifidobacterium*.

Next, 100 g of the hard capsule thus prepared was placed in a tumbling granulator, and a solution prepared by dissolving 10 g of shellac and 1 g of castor oil in 400 g of a mixture of methanol and ethyl acetate (volume ratio 1:1) was sprayed onto the entire surface of the hard capsule to a coating thickness of 0.3 mm, in order to prepare 100 g of the hard capsule with acid resistant coating (enteric *bifidobacterium*-containing hard capsule).

30 dialysis patients ingested 1 capsule of the enteric *bifidobacterium*-containing hard capsule thus prepared daily under the same conditions of ingestion as in Example 1. Blood was collected before and 4 weeks after the beginning of the ingestion of the enteric *bifidobacterium*-containing hard capsule, and blood phosphorus levels were measured. Table 6 shows the results.

For 15 patients who did not take either the enteric *bifidobacterium*-containing soft capsules or any other blood phosphorus level lowering agents (control group), the average blood phosphorus level before treatment was about 7.02 mg/dL, and the average blood phosphorus level four-week after treatment was about 8.01 mg/dL (for the control group, the average increase in blood phosphorus level was 0.99 mg/dL).

TABLE 6

| | Blood phosphorus level (mg/dL) | |
|---|---|---|
| | Before ingestion | 4 weeks after the beginnig of ingestion |
| Patient 1 | 6.3 | 4.9 |
| Patient 2 | 7.0 | 5.8 |
| Patient 3 | 6.1 | 4.9 |
| Patient 4 | 5.6 | 4.4 |
| Patient 5 | 7.4 | 6.2 |
| Patient 6 | 7.6 | 6.6 |
| Patient 7 | 7.5 | 6.7 |
| Patient 8 | 8.0 | 7.4 |
| Patient 9 | 6.6 | 6.0 |
| Patient 10 | 6.2 | 5.7 |
| Patient 11 | 7.0 | 6.5 |
| Patient 12 | 6.5 | 6.1 |
| Patient 13 | 6.6 | 6.3 |
| Patient 14 | 5.8 | 5.6 |
| Patient 15 | 6.0 | 5.9 |
| Patient 16 | 6.7 | 6.6 |
| Patient 17 | 8.2 | 8.3 |
| Patient 18 | 6.8 | 7.0 |
| Patient 19 | 6.9 | 7.3 |
| Patient 20 | 5.8 | 6.3 |

TABLE 6-continued

| | Blood phosphorus level (mg/dL) | |
|---|---|---|
| | Before ingestion | 4 weeks after the beginnig of ingestion |
| Patient 21 | 7.1 | 7.7 |
| Patient 22 | 7.4 | 7.9 |
| Patient 23 | 7.8 | 8.5 |
| Patient 24 | 8.3 | 9.0 |
| Patient 25 | 7.5 | 8.3 |
| Patient 26 | 8.2 | 9.1 |
| Patient 27 | 6.9 | 8.1 |
| Patient 28 | 6.2 | 7.4 |
| Patient 29 | 7.0 | 8.4 |
| Patient 30 | 7.4 | 9.0 |

Rate of patients with reduced blood phosphorus level: 53% (16 patients)
Average increase in blood phosphorus level for patients 1 to 30: 0.01 mg/dL
Average increase in blood phosphorus level for control group: 0.99 mg/dL As shown in Table 6, it can be understood that 16 (patients 1 to 16) of the 30 patients had lowered blood phosphorus levels after the ingestion of the enteric *bifidobacterium*-containing hard capsule. On the other hand, lowering of the blood phosphorus level was not observed after the ingestion of the enteric *bifidobacterium*-containing hard capsule for the remaining 14 patients. The average increase in blood phosphorus level was 0.01 mg/dL for the 30 patients compared to the increment for the control group of 0.99 mg/dL, and it can be understood that a blood phosphorus level elevation was inhibited.

For the control group, the blood phosphorus levels after treatment were significantly higher than the levels before treatment (Paired T-test: $p<0.01$), although no significant increase was observed in the treated group. Therefore, it can be understood that the enteric *bifidobacterium*-containing hard capsule obtained in Example 4 significantly inhibit a blood phosphorus level elevation.

Example 5

In order to prepare the *Bifidobacterium*-containing seamless capsule, the procedure was followed as in Example 1 except that the powder of killed *bifidobacterium* (*Bifidobacterium longum* subspecies *longum* JCM1217) cells was prepared by treating 100 g of the powder of the viable cells at 500 W for 10 minutes in a microwave oven.

30 dialysis patients ingested 0.2 g of the dead *bifidobacterium*-containing seamless capsule thus prepared daily under the same conditions of ingestion as in Example 1. Blood was collected before and 4 weeks after the beginning of the ingestion of the dead *bifidobacterium*-containing seamless capsule, and blood phosphorus levels were measured. Table 7 shows the results.

For 15 patients who did not take either the killed *bifidobacterium*-containing seamless capsules or any other blood phosphorus level lowering agents (control group), the average blood phosphorus level before treatment was about 7.19 mg/dL, and the average blood phosphorus level four-week after treatment was about 8.55 mg/dL (for the control group, the average increase in blood phosphorus level was 1.36 mg/dL).

TABLE 7

| | Blood phosphorus level (mg/dL) | |
|---|---|---|
| | Before ingestion | 4 weeks after the beginnig of ingestion |
| Patient 1 | 6.6 | 6.4 |
| Patient 2 | 5.6 | 5.4 |
| Patient 3 | 7.7 | 7.5 |
| Patient 4 | 6.2 | 6.1 |
| Patient 5 | 7.9 | 7.9 |
| Patient 6 | 6.3 | 6.4 |
| Patient 7 | 7.8 | 7.9 |
| Patient 8 | 6.5 | 6.6 |
| Patient 9 | 7.9 | 8.1 |
| Patient 10 | 8.3 | 8.6 |
| Patient 11 | 7.7 | 8.0 |
| Patient 12 | 8.4 | 8.7 |
| Patient 13 | 6.5 | 6.9 |
| Patient 14 | 6.9 | 7.4 |
| Patient 15 | 7.4 | 8.4 |
| Patient 16 | 5.7 | 6.7 |
| Patient 17 | 7.5 | 8.7 |
| Patient 18 | 8.1 | 9.3 |
| Patient 19 | 5.9 | 7.3 |
| Patient 20 | 6.8 | 8.3 |
| Patient 21 | 6.5 | 8.0 |
| Patient 22 | 5.5 | 7.1 |
| Patient 23 | 5.8 | 7.4 |
| Patient 24 | 7.8 | 9.6 |
| Patient 25 | 8.3 | 10.1 |
| Patient 26 | 7.8 | 9.8 |
| Patient 27 | 6.1 | 8.2 |
| Patient 28 | 8.3 | 10.4 |
| Patient 29 | 7.4 | 9.7 |
| Patient 30 | 8.3 | 10.9 |

Rate of patients with reduced blood phosphorus level: 13% (4 patients)
Average increase in blood phosphorus level for patients 1 to 30: 0.94 mg/dL
Average increase in blood phosphorus level for control group: 1.36 mg/dL As shown in Table 7, it can be understood that 4 (patients 1 to 4) of the 30 patients had lowered blood phosphorus levels after the ingestion of the killed *bifidobacterium*-containing seamless capsule. On the other hand, lowering of the blood phosphorus level was not observed after the ingestion of the killed *bifidobacterium*-containing seamless capsule for the remaining 26 patients. The average increase in blood phosphorus level was 0.94 mg/dL for the 30 patients compared to the increment for the control group of 1.36 mg/dL, and it can be understood that a blood phosphorus level elevation was inhibited.

Example 6

30 dialysis patients ingested the cell powder of *bifidobacterium* (*Bifidobacterium longum* subspecies *longum* JCM1217) as used in Example 1 without encapsulation in 2 billion cells of *bifidobacterium* daily over 4 weeks. The condition of ingestion was the same as that in Examples 1. The patients did not take any other blood phosphorus level lowering agents. While under dietary instructions by a dietitian, not all patients had the same meals. Blood was collected before and 4 weeks after the beginning of the ingestion of the cell powder of *bifidobacterium*, and blood phosphorus levels were measured. Table 8 shows the results.

For 15 patients who did not take either the cell powder of *bifidobacterium* or any other blood phosphorus level lowering agents (control group), the average blood phosphorus level before treatment was about 6.75 mg/dL, and the average blood phosphorus level four-week after treatment was about 7.97 mg/dL (for the control group, the average increase in blood phosphorus level was 1.21 mg/dL).

TABLE 8

| | Blood phosphorus level (mg/dL) | |
|---|---|---|
| | Before ingestion | 4 weeks after the beginnig of ingestion |
| Patient 1 | 6.3 | 6.1 |
| Patient 2 | 6.3 | 6.2 |
| Patient 3 | 5.9 | 5.9 |
| Patient 4 | 8.0 | 8.0 |
| Patient 5 | 6.3 | 6.4 |
| Patient 6 | 5.7 | 5.9 |
| Patient 7 | 7.8 | 8.2 |
| Patient 8 | 6.3 | 6.7 |
| Patient 9 | 7.2 | 7.7 |
| Patient 10 | 6.6 | 7.2 |
| Patient 11 | 7.7 | 8.4 |
| Patient 12 | 6.3 | 7.0 |
| Patient 13 | 8.5 | 9.2 |
| Patient 14 | 8.3 | 9.2 |
| Patient 15 | 7.0 | 8.3 |
| Patient 16 | 7.8 | 9.1 |
| Patient 17 | 5.9 | 7.3 |
| Patient 18 | 7.2 | 8.6 |
| Patient 19 | 6.3 | 7.7 |
| Patient 20 | 8.2 | 9.7 |
| Patient 21 | 7.7 | 9.3 |
| Patient 22 | 6.5 | 8.3 |
| Patient 23 | 8.1 | 10.1 |
| Patient 24 | 8.5 | 10.6 |
| Patient 25 | 7.4 | 9.6 |
| Patient 26 | 6.8 | 9.0 |
| Patient 27 | 5.6 | 7.9 |
| Patient 28 | 8.1 | 10.4 |
| Patient 29 | 6.4 | 8.7 |
| Patient 30 | 5.5 | 8.1 |

Rate of patients with reduced blood phosphorus level: 7% (2 patients)
Average increase in blood phosphorus level for patients 1 to 30: 1.15 mg/dL
Average increase in blood phosphorus level for control group: 1.21 mg/dL As shown in Table 8, it can be understood that 2 (patients 1 and 2) of the 30 patients had lowered blood phosphorus levels after the ingestion of the cell powder of *bifidobacterium*. On the other hand, lowering of the blood phosphorus level was not observed after the ingestion of the cell powder of *bifidobacterium* for the remaining 28 patients. The average increase in blood phosphorus level was 1.15 mg/dL for the patients compared to the increment for the control group of 1.21 mg/dL, and it can be understood that a blood phosphorus level elevation was inhibited slightly.

Example 7

In order to prepare the *Bifidobacterium*-containing seamless capsule, the procedure was followed as in Example 1 except that the cell powder of *bifidobacterium* (*Bifidobacterium bifidum* JCM1255) was used in place of that of *bifidobacterium* (*Bifidobacterium longum* subspecies *longum* JCM1217).

20 dialysis patients ingested 0.2 g of the *bifidobacterium*-containing seamless capsule thus prepared daily under the same conditions of ingestion as in Example 1. Blood was collected before and 4 weeks after the beginning of the ingestion of the *bifidobacterium*-containing seamless capsule, and blood phosphorus levels were measured. Table 9 shows the results.

For 15 patients who did not take either the cell powder of *bifidobacterium* or any other blood phosphorus level lowering agents (control group), the average blood phosphorus level before treatment was about 6.75 mg/dL, and the average blood phosphorus level four-week after treatment was about 7.97 mg/dL (for the control group, the average increase in blood phosphorus level was 1.21 mg/dL).

TABLE 9

| | Blood phosphorus level (mg/dL) | |
|---|---|---|
| | Before ingestion | 4 weeks after the beginnig of ingestion |
| Patient 1 | 5.93 | 3.87 |
| Patient 2 | 6.47 | 5.10 |
| Patient 3 | 7.04 | 6.25 |
| Patient 4 | 6.36 | 5.62 |
| Patient 5 | 6.61 | 6.06 |
| Patient 6 | 5.91 | 5.40 |
| Patient 7 | 8.39 | 7.97 |
| Patient 8 | 7.13 | 6.75 |
| Patient 9 | 6.31 | 5.96 |
| Patient 10 | 6.65 | 6.47 |
| Patient 11 | 7.21 | 7.23 |
| Patient 12 | 7.06 | 7.25 |
| Patient 13 | 6.28 | 6.49 |
| Patient 14 | 6.44 | 6.69 |
| Patient 15 | 7.03 | 7.36 |
| Patient 16 | 6.56 | 6.92 |
| Patient 17 | 5.48 | 6.11 |
| Patient 18 | 6.38 | 7.03 |
| Patient 19 | 8.21 | 9.04 |
| Patient 20 | 5.10 | 6.46 |

Rate of patients with reduced blood phosphorus level: 50% (10 patients)
Average increase in blood phosphorus level for patients 1 to 20: 0.13 mg/dL
Average increase in blood phosphorus level for control group: 1.21 mg/dL As shown in Table 9, it can be understood that 10 (patients 1 to 10) of the 20 patients had lowered blood phosphorus levels after the ingestion of the *bifidobacterium*-containing seamless capsule. On the other hand, lowering of the blood phosphorus level was not observed after the ingestion of the *bifidobacterium*-containing soft capsule for the remaining 10 patients. The average increase in blood phosphorus level was 0.13 mg/dL for the 20 patients compared to the increment for the control group of 1.21 mg/dL, and it can be understood that a blood phosphorus level elevation was inhibited.

For the control group, the blood phosphorus levels after treatment were significantly higher than the levels before treatment (Paired T-test: $p<0.01$), although no significant increase was observed in the treated group. Therefore, it can be understood that the *bifidobacterium*-containing seamless capsule obtained in Example 7 significantly inhibit a blood phosphorus level elevation.

Example 8

In order to prepare the seamless capsule containing lactic acid bacterium, the procedure was followed as in Example 1 except that the cell powder of lactic acid bacterium (*Lactobacillus acidophilus* JCM1132) was used in place of that of *bifidobacterium* (*Bifidobacterium longum* subspecies *longum* JCM1217).

20 dialysis patients ingested 0.2 g of the lactic acid bacterium-containing seamless capsule thus prepared daily under the same conditions of ingestion as in Example 1. Blood was collected before and 4 weeks after the beginning of the ingestion of the lactic acid bacterium-containing seamless capsule, and blood phosphorus levels were measured. Table 10 shows the results.

For 15 patients who did not take either the cell powder of lactic acid bacterium or any other blood phosphorus level lowering agents (control group), the average blood phosphorus level before treatment was about 6.75 mg/dL, and the average blood phosphorus level four-week after treatment was about 7.97 mg/dL (for the control group, the average increase in blood phosphorus level was 1.21 mg/dL).

TABLE 10

| | Blood phosphorus level (mg/dL) | |
|---|---|---|
| | Before ingestion | 4 weeks after the beginnig of ingestion |
| Patient 1 | 6.17 | 4.48 |
| Patient 2 | 6.61 | 5.21 |
| Patient 3 | 5.74 | 4.50 |
| Patient 4 | 8.79 | 7.63 |
| Patient 5 | 7.13 | 6.45 |
| Patient 6 | 6.55 | 5.90 |
| Patient 7 | 6.43 | 6.00 |
| Patient 8 | 7.24 | 7.04 |
| Patient 9 | 8.92 | 8.76 |
| Patient 10 | 6.44 | 6.47 |
| Patient 11 | 7.07 | 7.23 |
| Patient 12 | 6.20 | 6.43 |
| Patient 13 | 5.76 | 6.05 |
| Patient 14 | 6.77 | 7.29 |
| Patient 15 | 5.69 | 6.30 |
| Patient 16 | 7.12 | 7.74 |
| Patient 17 | 6.29 | 6.95 |
| Patient 18 | 6.30 | 7.00 |
| Patient 19 | 6.15 | 7.56 |
| Patient 20 | 5.18 | 6.73 |

Rate of patients with reduced blood phosphorus level: 45% (9 patients)
Average increase in blood phosphorus level for patients 1 to 20: 0.04 mg/dL
Average increase in blood phosphorus level for control group: 1.21 mg/dL As shown in Table 10, it can be understood that 9 (patients 1 to 9) of the 20 patients had lowered blood phosphorus levels after the ingestion of the lactic acid bacterium-containing seamless capsule. On the other hand, lowering of the blood phosphorus level was not observed after the ingestion of the lactic acid bacterium-containing seamless capsule for the remaining 11 patients. The average increase in blood phosphorus level was 0.04 mg/dL for the 20 patients compared to the increment for the control group of 1.21 mg/dL, and it can be understood that a blood phosphorus level elevation was inhibited.

For the control group, the blood phosphorus levels after treatment were significantly higher than the levels before treatment (Paired T-test: $p<0.01$), although no significant increase was observed in the treated group. Therefore, it can be understood that the lactic acid bacterium-containing seamless capsule obtained in Example 8 significantly inhibit a blood phosphorus level elevation.

Examples 9 to 17

Except that the cell powders of bifidobacterium (Bifidobacterium bifidum JCM1255: Example 9), bifidobacterium (Bifidobacterium animalis JCM10602: Example 10), bifidobacterium (Bifidobacterium infantis JCM7007: Example 11), bifidobacterium (Bifidobacterium dentium JCM1195: Example 12), lactic acid bacterium (Lactobacillus casei JCM1134: Example 13), lactic acid bacterium (Lactobacillus plantarum JCM11125: Example 14), lactic acid bacterium (Lactococcus lactis subspecies lactis JCM7638: Example 15), lactic acid bacterium (Enterococcus faecium JCM5804: Example 16), and lactic acid bacterium (Enterococcus faecalis JCM5803: Example 17) were used in place of that of bifidobacterium (Bifidobacterium longum subspecies longum JCM1217), the procedure was followed as in Example 1 in order to prepare the seamless capsule containing Bifidobacterium or lactic acid bacterium.

20 dialysis patients ingested 0.2 g of the seamless capsule containing bifidobacterium or lactic acid bacterium thus prepared daily under the same conditions of ingestion as in Example 1. Blood was collected before and 4 weeks after the beginning of the ingestion of the seamless capsule containing bifidobacterium or lactic acid bacterium, and blood phosphorus levels were measured. Table 11 shows the results.

TABLE 11

| | Name of strain used | Rate of the patients with reduced blood phosphorus level (%) | Average increase in blood phosphorus level (mg/dL) |
|---|---|---|---|
| Example 9 | Bifidobacterium bifidum JCM1255 | 55 | −0.02 |
| Example 10 | Bifidobacterium animalis JCM10602 | 50 | −0.10 |
| Example 11 | Bifidobacterium infantis JCM7007 | 40 | 0.01 |
| Example 12 | Bifidobacterium dentium JCM1195 | 40 | 0.19 |
| Example 13 | Lactobacillus casei JCM1134 | 35 | 0.62 |
| Example 14 | Lactobacillus plantarum JCM11125 | 35 | 0.45 |
| Example 15 | Lactococcus lactis subspecies lactis JCM7638 | 35 | 0.14 |
| Example 16 | Enterococcus faecium JCM5804 | 45 | 0.21 |
| Example 17 | Enterococcus faecalis JCM5803 | 30 | 0.26 |

Average increase in blood phosphorus level for control group: 1.32 mg/dL

For 15 patients who did not take either bifidobacterium or lactic acid bacterium or any other blood phosphorus level lowering agents (control group), the average blood phosphorus level before treatment was about 6.48 mg/dL, and the average blood phosphorus level four-week after treatment was about 7.59 mg/dL (for the control group, the average increase in blood phosphorus level was 1.32 mg/dL).

As shown in Table 11, it can be understood that Examples 9 and 10 had lowered blood phosphorus levels after the ingestion of the seamless capsule containing bifidobacterium. On the other hand, lowering of the blood phosphorus level was not observed after the ingestion of the seamless capsule containing bifidobacterium or lactic acid bacterium for Examples 11 to 17. Compared to the increment for the control group of 1.32 mg/dL, it can be understood that a blood phosphorus level elevation was inhibited.

For the control group, the blood phosphorus levels after treatment were significantly higher than the levels before treatment (Paired T-test: $p<0.01$), although no significant increase was observed in the treated group. Therefore, it can be understood that the bacterium- or the lactic acid bacterium-containing seamless capsule obtained in Examples 9 to 16 significantly inhibit a blood phosphorus level elevation.

It is clear from the experimental results presented above that the lactic acid bacteria have the effect of inhibit a blood phosphorus level elevation. Furthermore, it can be understood that the lactic acid bacteria, when ingested in the form of an enteric capsule, remarkably inhibit a blood phosphorus level elevation.

INDUSTRIAL APPLICABILITY

The inhibitor for blood phosphorus level elevation of the present invention is highly safe, is readily administrable, and can sufficiently inhibit a blood phosphorus level elevation. Therefore, the inhibitor for blood phosphorus level elevation of the present invention is applicable to a food product, a nutritional supplement, or the like that can inhibit a blood phosphorus level elevation for people such as dialysis patients and patients with impaired renal function.

The invention claimed is:

1. A method for treating blood phosphorus level elevation, comprising administering to a patient in need thereof one or more capsules each of which consists of a three layer seamless capsule, wherein each capsule has an average diameter of 1.5 mm to 8 mm, wherein a lactic acid bacterium is in a core of each capsule, as an active ingredient, wherein the lactic acid bacterium is at least one selected from the group consisting of *Bifidobacterium bifidum, B. longum, B. infantis, B. animalis, B. pseudolongum, B. dentium*.

2. A method for treating blood phosphorus level elevation according to claim 1, wherein the capsule is in an oral dosage form.

3. A method for treating blood phosphorus level elevation according to claim 1, wherein the capsule has acid resistance.

4. A method for treating blood phosphorus level elevation according to claim 1, wherein the capsule is enteric.

5. A method for treating blood phosphorus level elevation according to claim 1, further comprising encapsulating a composition comprising the lactic acid bacterium in each capsule prior to the administering.

6. A method for treating blood phosphorus level elevation according to claim 5, wherein in the encapsulating, no oligosaccharide is added to the composition.

7. A method for treating blood phosphorus level elevation according to claim 1, wherein the core of the capsule is free of oligosaccharide.

* * * * *